United States Patent [19]

Vembu et al.

[11] Patent Number: 5,639,501
[45] Date of Patent: Jun. 17, 1997

[54] SEPARATION OF MINERALS FROM WHEY PERMEATE

[76] Inventors: Rajan Vembu, 5908 Schumann Dr., Madison, Wis. 53711; V. Rathinam, 2633 20th Ave., Monroe, Wis. 53566

[21] Appl. No.: 380,986

[22] Filed: Jan. 31, 1995

[51] Int. Cl.⁶ .................... A23C 21/00; A23C 1/00; A23C 9/00; A61K 35/20
[52] U.S. Cl. .................... 426/583; 424/464; 424/535; 426/580; 426/443
[58] Field of Search .................... 426/580, 583, 426/443; 424/535, 464

[56] References Cited

U.S. PATENT DOCUMENTS

| | | | |
|---|---|---|---|
| 2,377,624 | 6/1945 | Gordon | 260/112 |
| 3,560,219 | 2/1971 | Attberry | 99/57 |
| 3,637,643 | 1/1972 | Wingerd | 260/122 |
| 3,864,506 | 2/1975 | Grindstaff et al. | 426/356 |
| 4,043,990 | 8/1977 | Melachouris | 260/112 R |
| 4,400,315 | 8/1983 | Thomas | 260/112 R |
| 4,963,387 | 10/1990 | Nakagawa et al. | 426/649 |
| 5,185,166 | 2/1993 | Nakagawa et al. | 426/74 |
| 5,352,476 | 10/1994 | Brule et al. | 426/657 |

*Primary Examiner*—David M. Naff
*Attorney, Agent, or Firm*—Quarles & Brady

[57] ABSTRACT

A process for extracting milk minerals from a whey product such as whey permeate or delactosed whey permeate is disclosed. The pH of the whey product is adjusted to a pH in the range of about 7.0 to 7.6. A phosphate compound is added to the whey product in an amount such that the weight percent of phosphate added to the whey product based on dry matter solids of the whey product is in the range of about 0.015–0.05%, and preferably in the range of about 0.025–0.03%. Suitable phosphates include pyrophosphate or tetrasodium pyrophosphate (TSPP). After the phosphate is added, the whey product/phosphate mixture is heated to a temperature in the range of about 145°–175° F. The whey product/phosphate mixture is maintained at a temperature in the range of about 145°–165° F. for a period of time sufficient to flocculate mineral solids from the whey product/ phosphate mixture. The flocculated mineral solids are then separated from liquids in the whey product/phosphate mixture, and the separated flocculated mineral solids are dried. Prior to drying, the flocculated mineral solids may be purified.

12 Claims, No Drawings

SEPARATION OF MINERALS FROM WHEY PERMEATE

FIELD OF THE INVENTION

The present invention relates generally to a process of treating whey. Specifically, the present invention relates to a process of extracting milk minerals from whey products such as whey permeate and delactosed whey permeate.

BACKGROUND OF THE INVENTION

In the United States and other milk-producing countries, milk is primarily used to manufacture cheese. However, only approximately half of the solids present in milk are coagulated and recovered as cheese; the remaining half are recovered as whey, a by-product of the cheese manufacturing process. Whey contains proteins, a milk sugar known as lactose, minerals and vitamins.

The treatment and disposal of whey frequently poses significant environmental problems. Whey is sometimes dried to be used as an extender in cattle feed, or in other processed food items such as candy bars. However, use in food applications is limited because of the high ash content of whey.

Using the more advanced technique of ultrafiltration, commercially valuable proteins can be recovered from whey. In ultrafiltration, pressure is applied to a solution to force whey through a semipermeable membrane. The openings of the membrane are sized to pass all portions of the whey except the proteins, which become concentrated. Whey proteins have long been used as food ingredients and in pharmaceutical applications.

The material which passes through the membrane is called whey permeate, also known as liquid permeate. Whey permeate contains lactose, minerals and vitamins. Lactose, used in baby food, bakery and pharmaceuticals, is commonly produced from whey permeate by evaporating and crystallizing it. Unfortunately, the recovery of lactose from whey permeate results in the byproduct delactosed whey permeate, which contains unrecoverable lactose and protein, and the minerals and vitamins originally present in the whey permeate. This byproduct is difficult to handle, and is typically land-spread (which leads to runoff, resulting in serious pollution problems in lakes and rivers), landfilled or sold for cattle feed at a loss to the factory.

There has been a growing demand in the food and pharmaceutical industries for functional and nutritionally sound mineral sources to replace the traditional sources, which often provide minerals which are impure and not easily absorbed. Minerals serve a wide variety of essential physiological functions ranging from structural components of body tissues to essential components of many enzymes and other biological important molecules.

Minerals are classified as micronutrients or trace elements on the basis of the amount present in the body. The seven micronutrients (calcium, potassium, sodium, magnesium, phosphorus, sulphur and chloride) are present in the body in quantities of more than five grams. Trace elements, which include boron, copper, iron, manganese, selenium, and zinc are found in the body in quantities less than five grams.

The natural milk minerals, particularly calcium and phosphorus, are of tremendous importance in nutrition. These minerals are essential for proper teeth and bone formation, and skeletal structure development. Calcium is the mineral element believed to be most deficient in meals in the United States. Calcium intakes in excess of 300 mg per day are difficult to achieve in the absence of milk and dairy products in the diet. This is far below the recommended dietary allowance (RDA) for calcium (1000 mg per day for adults and children ages one to ten, 1200 mg per day for adolescents and pregnant and lactating women, which equates to about four glasses of milk per day).

In fact, it has been reported that the mean daily calcium intake for females over age 12 does not exceed 85 percent of the RDA. In addition, during the years of peak bone mass development (18 to 30), more than 66 percent of all U.S. women fail to consume the recommended amounts of calcium on any given day. After age 35, this percentage increases to over 75 percent.

Although the general public is not fully aware of the consequences of inadequate mineral intake over prolonged periods of time, there is considerable scientific evidence that low calcium intake is one of several contributing factors leading to osteoporosis. In addition, the dietary ratio of calcium to phosphorous (Ca:P) relates directly to bone health. A Ca to P ratio of 1:1 to 2:1 is recommended to enhance bone marrowization in humans. Such ratios are difficult to achieve absent an adequate dietary supply of milk and dairy products, or an adequate supply of calcium and other minerals for the lactose-intolerant segment of the population.

Presently, most calcium supplements are produced from mining, from bone meal, or from oyster shells. These sources of calcium contain impurities such as lead and arsenic. High levels of such impurities could be toxic to the human system. By contrast, such impurities are filtered out naturally by the bodies of milk-producing animals such as the cow, goat, or buffalo, so that milk secreted by such animals contains only a balanced and pure form of the milk minerals, including calcium, phosphorus, potassium, magnesium, iron, and other trace elements as essential nutrients.

There have been relatively few attempts in the past to extract minerals from milk and whey. J. N. DeWitt et al reported (in Soc. Dairy Tech., 30, 112 (1978)) that demineralization of whey using ion exchange resins, after adjustment of the whey pH to 4–6, resulted in formation of a precipitate containing 90 percent lipids, 99 percent bacteria, and 10 percent of the proteins originally present in the whey. U.S. Pat. No. 3,560,219 to Attberry reported that addition of 0.075 molal concentration of calcium ion to cheese whey at a pH above 6.0 and at 60° C. resulted in formation of a precipitate containing 19 percent protein, 38 percent ash, 24 percent lactose and 4.5 percent lipids on a dry weight basis. All the original fat in the whey was removed in the precipitate.

U.S. Pat. No. 5,185,166 to Nakagawa, et al., describes a process for the production of milk mineral concentrate and drink containing minerals. According to the Nakagawa process, the pH of whey is adjusted to 4 to 6, after which the whey is ultra-filtered through a membrane having a cutoff molecular weight of 40,000. The filtrate is then concentrated until the concentration of lactose reaches approximately 50 percent. The concentrate is allowed to stand for 10 to 12 hours at 0° to 20° C., after which time the concentrate is centrifuged to yield a milk mineral concentrate containing 25 to 35 percent ash. The Nakagawa concentrate contained only small amounts of milk minerals, for example, about 2–10% potassium, and about 2–5% calcium.

U.S. Pat. No. 4,400,315 to Thomas discloses a method to remove phosphates from deproteinized cheese whey to improve the handling characteristics of deproteinized whey used to produce lactose or hydrolyzed syrup. According to the Thomas method, the pH of deproteinized whey is adjusted to 6.4 to 7.0 (preferably 6.5 to 6.7) by adding calcium hydroxide or potassium hydroxide. The deproteinized whey is then heated to a temperature in the range of 150° to 180° F. and held at that temperature for about 4 hours. After the four hour holding period, calcium hydroxide is added to the heated deproteinized whey in an amount not to exceed 0.01% by weight based on the dry matter solids of the deproteinized whey. Calcium phosphates were precipitated from the deproteinized whey after the deproteinized whey was held for at least two hours to allow the mixture to cool down. The calcium phosphates undoubtedly contained minerals of unknown analysis, but were discarded as waste.

Whey permeate and delactosed whey permeate are an excellent source of natural milk minerals. It is clearly desirable to develop a process to extract milk minerals from whey products such as whey permeate and delactosed permeate, to provide a natural and readily absorbable source of such minerals, which heretofore have been discarded as wastes.

SUMMARY OF THE INVENTION

The present invention is a process for extracting milk minerals from a whey product such as whey permeate or delactosed whey permeate, or mixtures of whey permeate and delactosed whey permeate. The pH of the whey product is adjusted to a pH in the range of about 7.0 to 7.6. A phosphate compound is added to the whey product in an amount such that the weight percent of phosphate added to whey product, based on dry matter solids of the whey product, is in the range of about 0.015–0.05, and preferably in the range of about 0.025–0.03. Suitable phosphates include pyrophosphate or tetrasodium pyrophosphate (TSPP). After the phosphate solution is added, the whey product/phosphate mixture is heated to a temperature in the range of about 145°–175° F. The whey product/phosphate mixture is maintained at a temperature in the range of about 145°–165° F. for a period of time sufficient to flocculate the mineral solids from the whey product/phosphate mixture. The flocculated mineral solids are then separated from liquids in the whey product/phosphate mixture, and the separated flocculated mineral solids are purified and dried.

It is an object of the present invention to provide an efficient process for extracting milk minerals from whey products.

It is another object of the present invention to reduce the mineral content in whey products so that heat exchanger equipment used in the processing of whey products will not be fouled.

It is another object of the present invention to provide milk minerals as a balanced and earily absorbable nutritional supplement.

It is another object of the present invention to provide milk minerals as functional ingredients in the food and pharmaceutical industries.

It is another object of the present invention to reduce the volume of delactosed whey permeate which is land-spread.

It is another object of the present invention to increase the yield of lactose from whey products.

Other objects, advantages and features of the present invention will become apparent after examination of the specification and claims.

BRIEF DESCRIPTION OF THE INVENTION

The source materials for use in the process of the present invention include whey products derived from milk produced by animals such as cows, goats, and buffaloes. The whey products are produced from cheese wheys from hard and soft cheeses such as, for example, cheddar, swiss, cottage cheese, or mozzarella cheese wheys. Such whey products, preferably having a solids content ranging from about 4.5% to 26%, include, for example, whey permeate and delactosed whey permeate and mixtures of whey permeate and delactosed whey permeate. If the solids content of the whey product is too high, it can be diluted with hot water to achieve a solids content in the desired range. If, on the other hand, the solids content is too low (for example, 4.5%), the solids content of the whey product can be increased by reverse osmosis or similar water removal processes well known to those in the food and dairy industry, to a desired level, which is at least about 15%.

The preferred source material is whey permeate, which is produced when whey is subjected to ultrafiltration in standard industrial ultrafiltration modules to separate out protein solids. In the ensuing discussion of the present invention, whey permeate is used as the source material. It is to be understood that delactosed whey permeate can be used either in place of, or mixed with, whey permeate.

Whey permeate typically has a pH in the range of 5.2 to 6.4. Depending on the type of whey permeate used and its solids content, the pH must be adjusted to maximize the yield of mineral solids. Therefore, the first step in the present invention is to adjust the pH of the whey permeate to a pH in the range of approximately 7.0 to 7.6, preferably about 7.2. The pH is adjusted by adding a basic alkali compound such as potassium hydroxide, sodium hydroxide, calcium hydroxide or the like.

Prior to, simultaneous with, or after pH adjustment, a phosphate compound is added to the whey product in an amount such that the weight percent of phosphate added to whey product, based on dry matter solids of the whey product, is in the range of about 0.015–0.05, and preferably in the range of about 0.025–0.03. Suitable phosphates include pyrophosphate, tetrasodium pyrophosphate (TSPP) or functionally similar phosphates.

The phosphate compound is critical to the success of this process, because the phosphate keeps the milk minerals in solution and in suspension so that the minerals do not foul heat exchange equipment when the whey product/phosphate mixture is heated in later stages of the process phosphate-treated whey products such as whey permeate are crystal clear and free of any floating solids, thereby increasing the efficiency of heat exchange equipment used to process whey products. When whey products are processed without the addition of a phosphate compound, heat exchange equipment is often fouled by minerals in the whey products.

Next, the pH-adjusted whey permeate/phosphate mixture is heated to a temperature in the range of about 145° to 175° F., preferably approximately 165° F. The mixture is then allowed to cool to a temperature in the range of approximately 145° to 165° F., preferably about 155° F., and maintained, or incubated, at that temperature for a period of time up to one hour, preferably, approximately 20 to 35 minutes, to allow the minerals to separate. If the mixture is maintained at a temperature much above 165° F., the lactose in the mixture (which is recovered at a later step in the process) will be discolored to an unpalatable brown color.

During the incubation period, salts composed of divalent ions such as calcium and magnesium and their associated anions, chiefly phosphates, citrates, and sulfates, precipitate out. The tank is continuously agitated during incubation to prevent the precipitates from settling to the bottom of the tank.

After the incubation period, the solids are separated from the supernatant liquid by passing the mixture through a clarifier such as the Westfalia MSD Model clarifier. Alternatively, separators, decanters or similar separation equipment well known in the dairy industry may be used to separate out the solids.

In the clarifier, the precipitated mineral solids are separated and discharged at a rate between discharges controlled by a turbidity meter in the clear permeate. The turbidity meter provides an indication of when sludge (which contains the milk mineral solids) must be removed. The supernatant liquid from the clarifier can be further processed by concentrating, crystallizing, purifying, and drying it to produce lactose.

The sludge discharged from the clarifier often has a high lactose content, sometimes up to 35% by weight. The mineral solids in the sludge can be directly spray-dried to produce a milk mineral product which would contain a high lactose content, and, by difference, a low minerals content.

Preferably, the milk mineral solids in the sludge are purified to reduce the lactose content, thereby increasing the percentage of milk minerals such as calcium and phosphorus. To purify the milk mineral solids, sludge discharged from the clarifier is mixed with hot water (for example, water at approximately 170° F.) and held under agitation in the mixing tank for about 20–30 minutes. The lactose-containing liquid is then separated from the mineral solids in a second separation operation using equipment such as separator, a decanter, or a second clarifier; the supernatant liquid from the separator can be added to the supernatant liquid stream from the clarifier for further processing, as described above.

If desired, additional phosphate compound (in accordance with the weight percent range disclosed above) can be added to the discharged mineral solids during the purification step, to pull out additional minerals from the residual lactose. In addition, pH can be adjusted if necessary by adding calcium hydroxide or similar compounds.

Purified mineral solids discharged from the separator in the second separation operation can be analyzed for calcium content. If the calcium content of the purified mineral solids is less than desired (for example, less than 25%), the calcium content can be increased by recycling the purified mineral solids back to the purifying tank, to mix them with hot water under agitation as described above, and then proceed through the second separator again.

The purified mineral solids discharged from the second separator are then dried, for example, by spray drying the minerals at an outlet temperature in the range of 180°–190° F. using a spray or rotary atomizer. The purified and dried milk mineral solids will typically contain at least 20% (by weight) calcium, at least 30% (by weight) phosphorus (in the form of phosphate), and numerous other minerals.

Because the calcium in the purified, dried milk mineral product is in the same form in which it occurs in milk (chiefly calcium phosphates and calcium citrates), calcium in the purified, dried milk mineral solids can be much more easily absorbed by humans than calcium in traditional calcium supplements in the form of calcium carbonate.

The easily absorbed purified, dried milk minerals can be further processed for application as nutritional supplements such as tablets, capsules, liquids, or the like, by the addition of carrier materials such as those commonly used to manufacture nutritional supplements. Such nutritional supplements have wide application as fortifiers for natural minerals in milk, baby food, confectionery, health foods, and calcium supplements. For example, nutritional supplements or compositions can be created which have as an active ingredient the purified, dried milk minerals. Such nutritional compositions will comprise the purified, dried milk minerals in admixture with a nutritionally acceptable non-toxic carrier or diluent. Examples of such carriers include lactose, glucose, and fructose. Flavoring can be added if desired.

In addition, the product produced by the present invention can be used as a functional ingredient in processed foods such as ham, sausage, and surimi (artificial seafood such as crab and lobster, which is manufactured by reformulating natural seafood with extenders). The mineral solids contain no fat, and hence, are able to counteract the de-foaming characteristics of fat globules present in common extenders such as whey protein concentrates, milk protein concentrates, and egg protein concentrates. Furthermore, the mineral solids product of the present invention can increase the calcium and mineral composition of such preparations, to enhance the nutritional value of the meat products, which are deficient in calcium and other minerals.

As shown from the results of the following Examples, purified, dried milk minerals produced according to the present invention contain at least 20% calcium and at least 30% phosphorus.

EXAMPLES

Example One

Concentrated cheese whey permeate having a solids content of 40%, resulting from ultrafiltration of cheese whey, was reconstituted with hot water to 26% total solids. The reconstituted whey permeate had a pH of about 5.4. The composition of the reconstituted whey permeate is provided in Table 1.

TABLE 1

Composition of Reconstituted Whey Permeate

|  | Weight Percent | Pounds |
| --- | --- | --- |
| Total Solids | 26.00 | 19,360 |
| Total Solids Composition |  |  |
| Protein | 0.85 | 633 |
| Fat | 0.00 | 0 |
| Ash | 2.28 | 1,698 |
| Lactose | 22.87 | 17,029 |
| B-galactoglobulin | 0.06 | 45 |
| Non-protein nitrogen | 0.79 | 58 |
| Sodium | 0.20 | 148 |
| Potassium | 0.65 | 484 |
| Calcium | 0.14 | 109 |
| Magnesium | 0.08 | 60 |
| Phosphorus | 0.17 | 126 |
| Chloride | 0.51 | 379 |

The mineral content of the whey permeate was determined by ashing the permeate at 550° C. in a Muffle Furnace, as described in the *Standard Methods for the Examination of Water and Wastewater*, 15th Edition, American Public Health (1980). The mineral elements potassium, calcium, magnesium, sodium, phosphorous, sulphur, boron, zinc, ferrous, and aluminum present in the permeate were then analyzed with an inductivity-coupled plasma emission (ICP) spectrophotometer. Nitrogen content of the permeate was determined by the micro Kjeldahl Method of protein analysis commonly used in the food industry.

Approximately 5.8 pounds of pyrophosphate was added to the reconstituted whey permeate, to achieve 0.03 weight percent phosphate based on dry matter solids of the reconstituted whey permeate. Sufficient food grade 40% sodium hydroxide was added to the whey permeate/phosphate mixture to bring the pH to approximately 7.2.

The mixture was heated to 170° F., then was allowed to cool to 156° F. and incubate at that temperature for 30 minutes to allow the solid mineral salts to precipitate out of the whey permeate/phosphate mixture. The mixture was under constant agitation during incubation to prevent the precipitated mineral solids from settling.

After the incubation period, the whey permeate/phosphate mixture was fed to a Westfalia Separator centrifugal clarifier rotating at 4850 RPM. The time between discharges from the clarifier of the precipitated salts was controlled by a turbidity meter in the clear permeate. This gave an indication of when the sludge capacity of the clarifier bowl was reached. Discharge intervals of 3 to 9 minutes were recorded at a separator feed rate of 14,250 pounds per hour of 23.5% solids.

The discharged sludge had an initial solids content of 14.2%. To purify the solids, water at a temperature of 170° F. was added to the sludge (containing the milk minerals) in order to dissolve and remove residual lactose and increase the mineral content. The diluted sludge was held under agitation in the tank for approximately 20 minutes. The resulting diluted sludge had a solids content of 8.2%. The solids and liquids in the diluted sludge were separated in a separator. After separation, the solids content increased to 24.4%. The supernatant liquid from the clarifier was concentrated, crystallized, and dried, yielding lactose.

The solid mineral product was dried in a conventional spray dryer having an outlet temperature of 180° F. to produce a moisture content between 2-5%.

The composition of the milk mineral powder produced from Example One is listed in Table 2. Analysis of the powder was accomplished in a similar manner to analysis of the whey permeate described above. As can be seen by a review of Table 2, the milk mineral powder is a good source of minerals (which are all present in the ash), containing, for example, 23% calcium and 38% phosphorus, plus a good distribution of other necessary minerals.

TABLE 2

| Composition of Milk Mineral Product | |
|---|---|
| | Weight Percent |
| Total Solids | 97.50% |
| Moisture | 2.50% |
| Total: | 100.00% |
| Total Solids Composition | |
| Protein | 2.57% |
| Fat | 0.00% |

TABLE 2-continued

| Composition of Milk Mineral Product | |
|---|---|
| | Weight Percent |
| Carbohydrate (as Lactose) | 10.00% |
| Milk Minerals (after ashing) | 73.77% |
| Sodium | 0.74% |
| Potassium | 10.03% |
| Calcium | 23.00% |
| Phosphorous | 38.00% |
| Magnesium | 1.60% |
| Chloride | 0.40% |
| Volatiles* | 11.16% |
| Trace Elements | |
| Boron | 3 PPM |
| Copper | 2 PPM |
| Iron | 150 PPM |
| Manganese | 3 PPM |
| Selenium | 7 PPM |
| Zinc | 25 PPM |

* = Elemental analysis for Calcium ions (+ charge) only and does not include the associated anions (− charges) such as oxide, chloride, carbonate, citrate and sulphate, which are also present but evaporate in the laboratory ashing procedure because they are volatile compounds in the milk minerals.

Example Two

The procedure described in Example One was followed in Example Two, except potassium hydroxide was substituted for sodium hydroxide, and the sludge discharged from the clarifier was washed with 145° F. water instead of 170° F. water.

Concentrated cheese whey permeate having a solids content of 40% was reconstituted with hot water to 24% total solids. The composition of the reconstituted whey permeate is provided in Table 3.

TABLE 3

| Composition of Reconstituted Whey Permeate | | |
|---|---|---|
| | Weight Percent | Pounds |
| Total Solids | 24.00 | 19,360 |
| Total Solids Composition | | |
| Protein | 0.95 | 766 |
| Fat | 0.00 | 0 |
| Ash | 2.18 | 1,760 |
| Lactose | 20.87 | 16,834 |
| B-galactoglobulin | 0.06 | 48 |
| Non-protein nitrogen | 0.86 | 694 |
| Sodium | 0.19 | 153 |
| Potassium | 0.64 | 516 |
| Calcium | 0.14 | 113 |
| Magnesium | 0.03 | 24 |
| Phosphorus | 0.16 | 129 |
| Chloride | 0.51 | 411 |

Approximately 5.8 pounds of pyrophosphate was added to the reconstituted whey permeate, to achieve 0.03 weight percent phosphate based on dry matter solids of the reconstituted whey permeate. Sufficient food grade 35% potassium hydroxide was added to the whey permeate/phosphate mixture to bring the pH to approximately 7.2.

The mixture was heated to 170° F., then was allowed to cool to 145° F. and incubate at that temperature for 30 minutes to allow the solid mineral salts to precipitate out of the whey permeate/phosphate mixture. The mixture was under constant agitation during incubation to prevent the precipitated mineral solids from settling.

After the incubation period, the whey permeate/phosphate mixture was fed to a Westfalia Separator centrifugal clarifier rotating at 4850 RPM. Sludge discharged from the clarifier was purified by diluting with 145° F. water and holding it under agitation for about 20 minutes to remove lactose and increase the calcium content. The solids and liquids in the diluted sludge were separated in a separator, and further processed as described in Example One.

The composition of the milk mineral powder produced from Example Two is listed in Table 4. As with the milk mineral powder produced in Example One, the milk mineral powder produced in Example Two is a good source of minerals (which are all present in the ash), containing, for example, 24% calcium and 37% phosphorus, in addition to a number of other essential minerals.

TABLE 4

Composition of Milk Mineral Product

|  | Weight Percent |
|---|---|
| Total Solids | 96.50% |
| Moisture | 3.50% |
| Total: | 100.00% |
| Total Solids Composition | |
| Protein | 3.0% |
| Fat | 0.0% |
| Carbohydrate (as Lactose) | 9.5% |
| Milk Minerals (after ashing) | 72.63% |
| Sodium | 0.69% |
| Potassium | 8.95% |
| Calcium | 24.00% |
| Phosphorous | 37.00% |
| Magnesium | 1.56% |
| Chloride | 0.43% |
| Volatiles* | 11.37% |

Trace Elements

| Boron | 3 PPM |
|---|---|
| Copper | 2 PPM |
| Iron | 150 PPM |
| Manganese | 3 PPM |
| Selenium | 7 PPM |
| Zinc | 25 PPM |

* = Elemental analysis for Calcium ions (+ charge) only and does not include the associated anions (− charges) such as oxide, chloride, carbonate, citrate and sulphate, which are also present but evaporate in the laboratory ashing procedure because they are volatile compounds in the milk minerals.

Example Three

The procedure followed in Example Two was used, except that approximately 0.8 pounds of pyrophosphate was added to the clarifier sludge when it was diluted, to achieve 0.05 weight percent phosphate based on dry matter solids of the clarifier sludge. The phosphate added to the clarifier sludge was in addition to the phosphate added initially, when the concentrated whey permeate was reconstituted to lower its solids content.

Example Three produced a milk mineral powder similar in composition to that produced in Example Two, as listed in Table 4.

In all Examples, the dried mineral powder was tested for minerals content (potassium, calcium, magnesium, sodium, phosphorous, sulphur, boron, zinc, iron, and aluminum), total nitrogen, solids, ash, and pH. The results of the tests indicated that the mineral powder contained all major minerals, namely calcium and potassium, and all minor minerals. The mineral powder was also tested for lead and arsenic; the results indicated that the later metals were present at less than toxic levels.

Example Four (Prophetic)

The procedure followed in Example Two will be used, except that the sludge discharged from the clarifier will be washed with 170° F. water instead of 145° F. water to increase the calcium and magnesium content of the mineral solids product. The higher water temperature will serve to reduce the lactose content because more of the sugar will dissolve in the higher temperature water. The expected composition of the milk mineral product produced in Example 4 is set forth in Table 5.

TABLE 5

Composition of Milk Mineral Product (Predicted)

|  | Weight Percent |
|---|---|
| Total Solids | 96.00% |
| Moisture | 4.00% |
| Total: | 100.00% |
| Total Solids Composition | |
| Protein | 3.5% |
| Fat | 0.0% |
| Carbohydrate (as Lactose) | 5.0% |
| Milk Minerals (after ashing) | 75.5% |
| Sodium | 0.70% |
| Potassium | 7.00% |
| Calcium | 27.50% |
| Phosphorous | 38.00% |
| Magnesium | 2.50% |
| Chloride | 0.40% |
| Volatiles* | 11.40% |

Trace Elements

| Boron | 3 PPM |
|---|---|
| Copper | 2 PPM |
| Iron | 150 PPM |
| Manganese | 3 PPM |
| Selenium | 7 PPM |
| Zinc | 25 PPM |

* = Volatile compounds which will be evaporated during laboratory analysis, such as oxides, will be accounted for by difference to be 8.4%.

Example Five

A milk mineral product was produced according to the procedure outlined in Example One, above. A nutritional composition was produced in the form of a 250 milligram tablet, using glucose and fructose as the carrier. The tablet contained 92% calcium in the form of calcium phosphate and calcium citrate. The composition of the tablet produced in Example Five is set forth in Table 6.

Tablet Composition

|  | Weight Percent | Milligrams |
|---|---|---|
| Calcium | 92.00 | 230 |
| Glucose | 4.00 | 10 |
| Protein Casein | 2.00 | 5 |

-continued

| Tablet Composition | | |
|---|---|---|
| | Weight Percent | Milligrams |
| Vitamins A, D, E and Flavorings | 1.20 | 3 |
| Fructose | .80 | 2 |
| | 100 | 250 |

It will be apparent to one of ordinary skill in the art that changes in modifications can be made to the above-described process without departing from the spirit or scope of the invention set forth herein.

We claim:

1. A process for extracting milk minerals from a whey permeate, the process consisting essentially of the steps of:
   a. adjusting the pH of a whey permeate from ultrafiltration having a solids content in a range of about 15% to 26% to a pH in the range of about 7.0 to 7.6;
   b. before or after step (a), adding to the whey permeate a pyrophosphate in an amount of about 0.015–0.05%, based on dry matter solids of the whey permeate to produce a whey permeate/pyrophosphate mixture;
   c. heating the whey permeate/pyrophosphate mixture from steps (a) and (b) to a temperature in the range of about 145–175 degrees F.;
   d. maintaining the whey permeate/pyrophosphate mixture from step (c) at a temperature in the range of about 145°–165 degrees F. for a period of time up to about one hour sufficient to flocculate mineral solids from the whey permeate/pyrophosphate mixture;
   e. separating the flocculated mineral solids from liquids in the whey permeate/pyrophosphate mixture to produce separated mineral solids; and
   f. drying the separated mineral solids.

2. The process as described in claim 1, further comprising the step of purifying the separated mineral solids.

3. The process as described in claim 2, wherein the separated mineral solids are purified prior to drying by diluting the separated mineral solids with hot water, agitating the diluted mineral solids, and separating the diluted mineral solids from the diluent.

4. The process as described in claim 3, wherein the pyrophosphate is tetrasodium pyrophosphate.

5. The process as described in claim 4, wherein the weight percent of pyrophosphate added to the whey permeate, based on dry matter solids of the whey permeate, is in the range of about 0.025–0.03%.

6. The process as described in claim 5, wherein the whey permeate/pyrophosphate mixture is maintained at a temperature in the range of about 145–165 degrees F. for approximately 20–35 minutes.

7. A milk mineral product produced from a whey permeate by the process consisting essentially of the steps of:
   a. adjusting the pH of a whey permeate from ultrafiltration having a solids content in a range of about 15% to 26% to a pH in the range of about 7.0 to 7.6;
   b. before or after step (a), adding to the whey permeate a pyrophosphate in an amount of about 0.015 to 0.05%, based on dry matter solids of the whey permeate to produce a whey permeate/pyrophosphate mixture;
   c. heating the whey permeate/pyrophosphate mixture from steps (a) and (b) to a temperature in the range of about 145–175 degrees F.;
   d. maintaining the whey permeate/pyrophosphate mixture from step (c) at a temperature in the range of about 145–165 degrees F. for a period of time up to about one hour sufficient to flocculate mineral solids from the whey permeate/pyrophosphate mixture;
   e. separating the flocculated mineral solids from liquids in the whey permeate/pyrophosphate mixture to produce separated mineral solids; and
   f. drying the separated mineral solids.

8. The product described in claim 7, wherein the process further comprises the step of purifying the separated mineral solids.

9. The product described in claim 8, wherein the separated mineral solids are purified prior to drying by diluting the separated mineral solids with hot water, agitating the diluted mineral solids, and separating the diluted mineral solids from the diluent.

10. The product described in claim 9, wherein the pyrophosphate is tetrasodium pyrophosphate.

11. The product described in claim 10, wherein the weight percent of pyrophosphate added to the whey permeate, based on dry matter solids of the whey permeate, is in the range of about 0.025–0.03%.

12. The product described in claim 11, wherein the whey permeate/pyrophosphate mixture is maintained at a temperature in the range of about 145–165 degrees F. for approximately 20–35 minutes.

\* \* \* \* \*